(12) United States Patent
Shin et al.

(10) Patent No.: US 12,307,693 B2
(45) Date of Patent: May 20, 2025

(54) AUTOMATED METHOD FOR ALIGNING THREE DIMENSIONAL DENTAL LIBRARY MODEL TO THREE DIMENSIONAL ORAL SCAN DATA AND COMPUTER READABLE MEDIUM HAVING PROGRAM FOR PERFORMING THE METHOD

(71) Applicant: IMAGOWORKS INC., Seoul (KR)

(72) Inventors: Bonjour Shin, Seoul (KR); Hannah Kim, Seoul (KR); Donguk Kam, Seoul (KR); Jinhyeok Choi, Seoul (KR); Tae-geun Son, Seoul (KR); Youngjun Kim, Seoul (KR)

(73) Assignee: IMAGOWORKS INC., Seoul (KR)

( * ) Notice: Subject to any disclaimer, the term of this patent is extended or adjusted under 35 U.S.C. 154(b) by 199 days.

(21) Appl. No.: 18/114,380

(22) Filed: Feb. 27, 2023

(65) Prior Publication Data
US 2023/0281840 A1 Sep. 7, 2023

(30) Foreign Application Priority Data

Mar. 4, 2022 (KR) .......................... 10-2022-0028316

(51) Int. Cl.
*G06T 7/33* (2017.01)
*G06T 7/10* (2017.01)
(Continued)

(52) U.S. Cl.
CPC ................ *G06T 7/344* (2017.01); *G06T 7/10* (2017.01); *G06T 19/20* (2013.01); *G16H 30/20* (2018.01);
(Continued)

(58) Field of Classification Search
None
See application file for complete search history.

(56) References Cited

U.S. PATENT DOCUMENTS

2009/0316966 A1* 12/2009 Marshall ................ G16H 50/30
382/128
2018/0085203 A1* 3/2018 Ramirez .................. A61C 5/77
(Continued)

FOREIGN PATENT DOCUMENTS

| JP | 2018-526035 A | 9/2018 |
|---|---|---|
| KR | 10-2020-0006506 A | 1/2020 |

(Continued)

OTHER PUBLICATIONS

Extended European search report dated on May 24, 2023.
(Continued)

*Primary Examiner* — Yingchun He
(74) *Attorney, Agent, or Firm* — LEEPI

(57) ABSTRACT

An automated method for aligning a 3D dental library model to 3D oral scan data includes determining a valid tooth of the 3D oral scan data, extracting scan landmarks of the 3D oral scan data, loading a dental library model corresponding to the valid tooth of the 3D oral scan data, extracting library landmarks of the 3D dental library model, initial-aligning the 3D dental library model to the 3D oral scan data using the scan landmarks and the library landmarks and matching an individual tooth of the 3D dental library model and an individual tooth of the 3D oral scan data.

15 Claims, 11 Drawing Sheets

(51) Int. Cl.
*G06T 19/20* (2011.01)
*G16H 30/20* (2018.01)

(52) U.S. Cl.
CPC ............... *G06T 2207/10028* (2013.01); *G06T 2207/20084* (2013.01); *G06T 2207/30036* (2013.01); *G06T 2210/41* (2013.01); *G06T 2219/2016* (2013.01)

(56) References Cited

U.S. PATENT DOCUMENTS

| | | | | |
|---|---|---|---|---|
| 2018/0303581 | A1* | 10/2018 | Martz | A61C 7/08 |
| 2019/0026910 | A1* | 1/2019 | Dekel | A61C 9/008 |
| 2022/0164954 | A1* | 5/2022 | Kim | G06T 7/70 |
| 2022/0165388 | A1* | 5/2022 | Chernov | A61B 5/004 |
| 2023/0048898 | A1* | 2/2023 | Cofar | A61C 13/0004 |
| 2023/0263605 | A1* | 8/2023 | Madden | A61C 13/34 264/16 |

FOREIGN PATENT DOCUMENTS

| | | |
|---|---|---|
| KR | 10-2020-0023703 A | 3/2020 |
| KR | 10-2273438 B1 | 6/2021 |
| KR | 10-2331034 B1 | 11/2021 |
| WO | 2021210966 A1 | 10/2021 |

OTHER PUBLICATIONS

Impact of number of registration points on the positional accuracy of a prosthetic treatment plan incorporated into a cone beam computed tomography scan by surface scan registration, Faris Z. Jamjoom, et al., Clin Oral Impl Res., 2019, 30, pp. 826-832.

How dose best fit alignment determine how the parts are aligned, Sep. 23, 2020, https://support.3dsystems.com/s/article/How-does-Best-Fit-Alignment-determine-how-the-parts-are-aligned?language=en_US.

* cited by examiner

AUTOMATED METHOD FOR ALIGNING THREE DIMENSIONAL DENTAL LIBRARY MODEL TO THREE DIMENSIONAL ORAL SCAN DATA AND COMPUTER READABLE MEDIUM HAVING PROGRAM FOR PERFORMING THE METHOD

PRIORITY STATEMENT

This application claims priority under 35 U.S.C. § 119 to Korean Patent Application No. 10-2022-0028316, filed on Mar. 4, 2022 in the Korean Intellectual Property Office (KIPO) and International Patent Application No. PCT/KR2022/003320 filed on Mar. 8, 2022, the contents of which are herein incorporated by reference in their entireties.

BACKGROUND

1. Technical Field

Embodiments relate to an automated method for aligning a three dimensional (3D) dental library model to 3D oral scan data and a non-transitory computer-readable storage medium having stored thereon program instructions of the automated method for aligning the 3D dental library model to the 3D oral scan data. More particularly, embodiments relate to an automated method for aligning a 3D dental library model to 3D oral scan data to reduce time and process of manufacturing prostheses, implants, braces and dental instruments and a non-transitory computer-readable storage medium having stored thereon program instructions of the automated method for aligning the 3D dental library model to the 3D oral scan data.

2. Description of the Related Art 3D oral scan data may refer to data scanned by a 3D scanner for teeth and oral cavity, an impression model of the teeth and the oral cavity or a reconstruction model of the teeth and the oral cavity. In dental treatment such as prosthetic treatment including in-ray, on-ray and crown, implant and orthodontics oral data of a patient may be obtained and may be used to design prostheses or implants and manufacture braces.

Conventionally, a method of manufacturing prostheses, implants, braces by hand after directly modeling the oral cavity using alginate or the like has been mainly used. Recently, a digital method including obtaining 3D oral scan data of a patient using the 3D scanner, designing prostheses, implants and braces using a computer, and 3D printing them has been gradually used.

In the digital method, a dental library model predesigned to some extent for each tooth type (tooth number) may be used. In order to digitally manufacture prostheses, implants and braces, the dental library model may be aligned to the 3D oral scan data. If the process of aligning the dental library model to the 3D oral scan data is performed manually, a work fatigue of the dentist or dental technician may increase and an accuracy and a productivity of the result may decrease.

SUMMARY

Embodiments provide an automated method for aligning a 3D dental library model to 3D oral scan data to reduce time and process of manufacturing prostheses, implants, braces and dental instruments.

Embodiments provide a non-transitory computer-readable storage medium having stored thereon program instructions of the automated method for aligning the 3D dental library model to the 3D oral scan data.

In an example automated method for aligning a 3D dental library model to 3D oral scan data according to the present inventive concept, the method includes determining a valid tooth of the 3D oral scan data, extracting scan landmarks of the 3D oral scan data, loading a dental library model corresponding to the valid tooth of the 3D oral scan data, extracting library landmarks of the 3D dental library model, initial-aligning the 3D dental library model to the 3D oral scan data using the scan landmarks and the library landmarks and matching an individual tooth of the 3D dental library model and an individual tooth of the 3D oral scan data.

In an embodiment, the automated method for aligning the 3D dental library model to 3D oral scan data method may further include segmenting teeth of the 3D oral scan data to generate teeth segmentation data.

In an embodiment, the initial-aligning the 3D dental library model to the 3D oral scan data may include matching a second arch formed by teeth of the 3D dental library model with a first arch formed by teeth of the 3D oral scan data.

In an embodiment, the scan landmarks may include at least three landmarks disposed in the 3D oral scan data. The library landmarks include at least three landmarks disposed in the 3D dental library model.

In an embodiment, the scan landmarks may include a first landmark disposed at a first end of a first arch formed by teeth of the 3D oral scan data, a second landmark disposed at a second end of the first arch and a third landmark disposed at a central point of the first arch. The library landmarks may include a fourth landmark disposed at a first end of a second arch formed by teeth of the 3D dental library model, a fifth landmark disposed at a second end of the second arch and a sixth landmark disposed at a central point of the second arch.

In an embodiment, the scan landmarks may include a first landmark disposed at a last tooth in a first end in a horizontal direction of the 3D oral scan data, a second landmark disposed at a last tooth in a second end in the horizontal direction of the 3D oral scan data and a third landmark disposed at a center of two central incisors of the 3D oral scan data. The library landmarks may include a fourth landmark disposed at a last tooth in a first end in a horizontal direction of the 3D dental library model, a fifth landmark disposed at a last tooth in a second end in the horizontal direction of the 3D dental library model and a third landmark disposed at a center of two central incisors of the 3D dental library model.

In an embodiment, the matching the individual tooth of the 3D dental library model and the individual tooth of the 3D oral scan data may include matching a center of the individual tooth of the 3D dental library model with a center of the individual tooth of the 3D oral scan data.

In an embodiment, the matching the individual tooth of the 3D dental library model and the individual tooth of the 3D oral scan data may include rotating the individual tooth of the 3D dental library model and adjusting a size of the individual tooth of the 3D dental library model to minimize a difference between an angle of the individual tooth of the 3D dental library model and an angle of the individual tooth of the 3D oral scan data and a difference between the size of the individual tooth of the 3D dental library model and a size of the individual tooth of the 3D oral scan data.

In an embodiment, the first neural network may be used in the determining the valid tooth of the 3D oral scan data. The second neural network different from the first neural network may be used in the extracting the scan landmarks of the 3D oral scan data.

In an embodiment, an input of the first neural network may be the 3D oral scan data and an output of the first neural network may be individual tooth information of the 3D oral scan data.

In an embodiment, the individual tooth information may be a scalar value or a labeling value expressed on the 3D oral scan data.

In an embodiment, an input of the first neural network may be the 3D oral scan data and an output of the first neural network may be teeth segmentation data of the 3D oral scan data including segmented teeth of the 3D oral scan data.

In an embodiment, an input of the second neural network may be the 3D oral scan data and an output of the second neural network may be 3D coordinates of the scan landmarks.

In an embodiment, the extracting the scan landmarks of the 3D oral scan data may include generating a 2D depth image based on the 3D oral scan data, extracting 2D coordinates of the scan landmarks from the 2D depth image using the second neural network and inverse-projecting the 2D coordinates to the 3D oral scan data.

In an embodiment, the second neural network may be used in the extracting the library landmarks of the 3D dental library model.

An example non-transitory computer-readable storage medium has stored thereon program instructions, which when executed by at least one hardware processor, performs determining a valid tooth of the 3D oral scan data, extracting scan landmarks of the 3D oral scan data, loading a dental library model corresponding to the valid tooth of the 3D oral scan data, extracting library landmarks of the 3D dental library model, initial-aligning the 3D dental library model to the 3D oral scan data using the scan landmarks and the library landmarks and matching an individual tooth of the 3D dental library model and an individual tooth of the 3D oral scan data.

According to the automated method for aligning the 3D dental library model to the 3D oral scan data, the process of aligning the 3D dental library model to the 3D oral scan data is performed automatically so that a work fatigue of the dentist or dental technician may decrease and an accuracy of the aligning result may increase.

In addition, the aligned dental library model may be used to manufacture prostheses, implants, braces and dental instruments so that an effort and a time of manufacturing the prostheses, the implants, the braces and the dental instruments may decrease and an accuracy and a productivity of the prostheses, the implants, the braces and the dental instruments may increase.

In addition, a deep learning may be used in some steps of the automated method for aligning the 3D dental library model to the 3D oral scan data. When the deep learning is be used in some steps, the work fatigue of the dentist or dental technician may further decrease and the accuracy of the aligning result may further increase.

BRIEF DESCRIPTION OF THE DRAWINGS

The above and other features and advantages of the present inventive concept will become more apparent by describing in detailed embodiments thereof with reference to the accompanying drawings, in which.

DETAILED DESCRIPTION OF THE EMBODIMENTS

Figure 1:
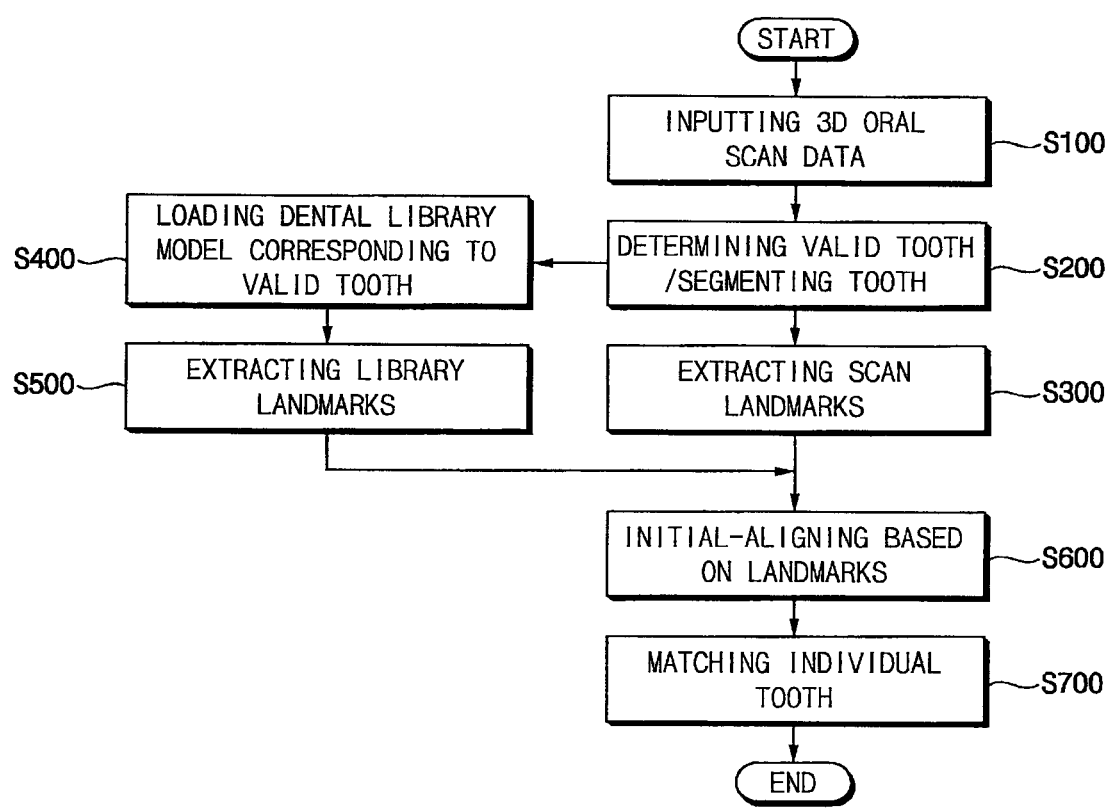
FIG. 1 is a flowchart diagram illustrating an automated method for aligning a 3D dental library model to 3D oral scan data according to an embodiment of the present inventive concept.

The present inventive concept now will be described more fully hereinafter with reference to the accompanying drawings, in which embodiments of the present invention are shown. The present inventive concept may, however, be embodied in many different forms and should not be construed as limited to the embodiments set forth herein.

Rather, these embodiments are provided so that this disclosure will be thorough and complete, and will fully convey the scope of the present invention to those skilled in the art. Like reference numerals refer to like elements throughout.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the inventive concept as used herein.

Hereinafter, the present inventive concept will be explained in detail with reference to the accompanying drawings.

Figure 2A:
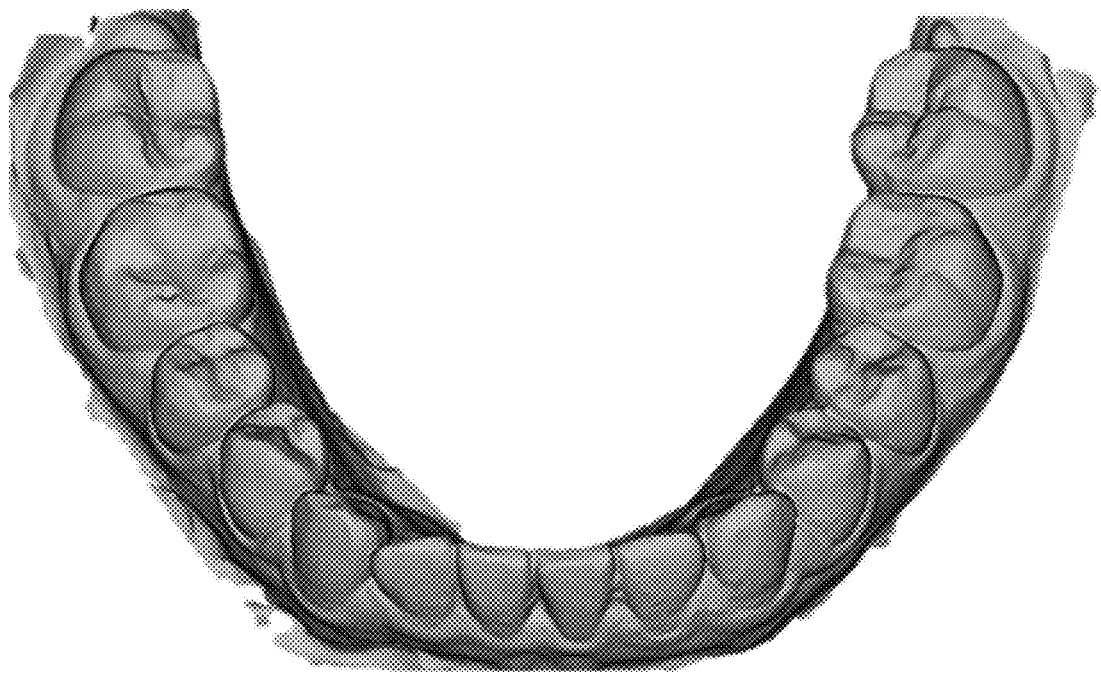
FIG. 2A is a perspective view illustrating an example of the 3D oral scan data.
Figure 2B:
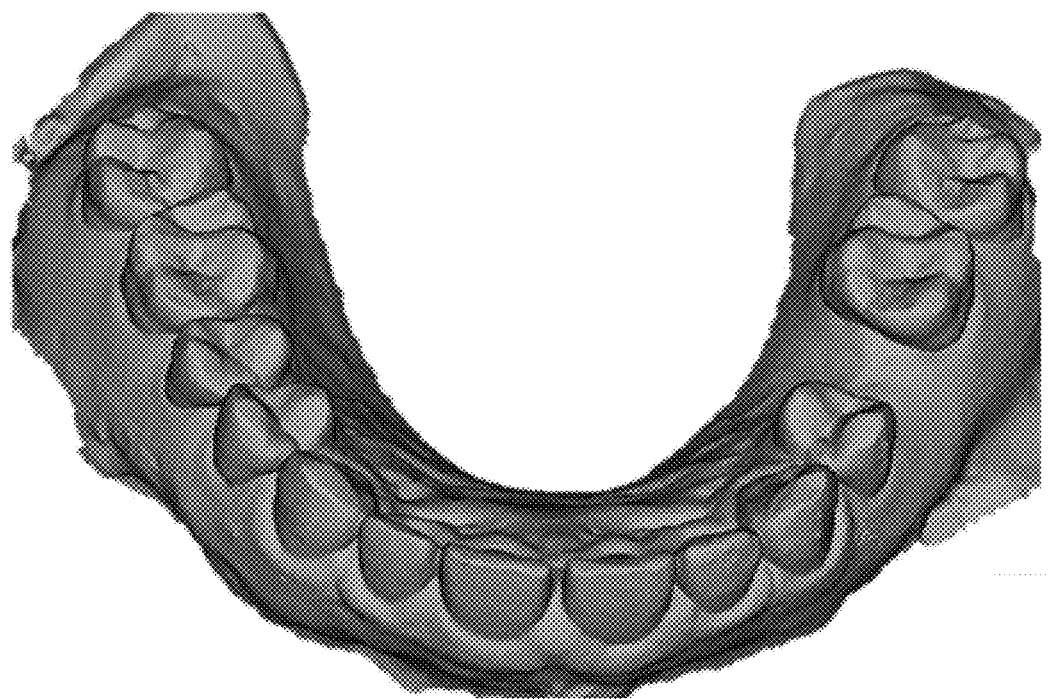
FIG. 2B is a perspective view illustrating an example of the 3D oral scan data.
Figure 3A:
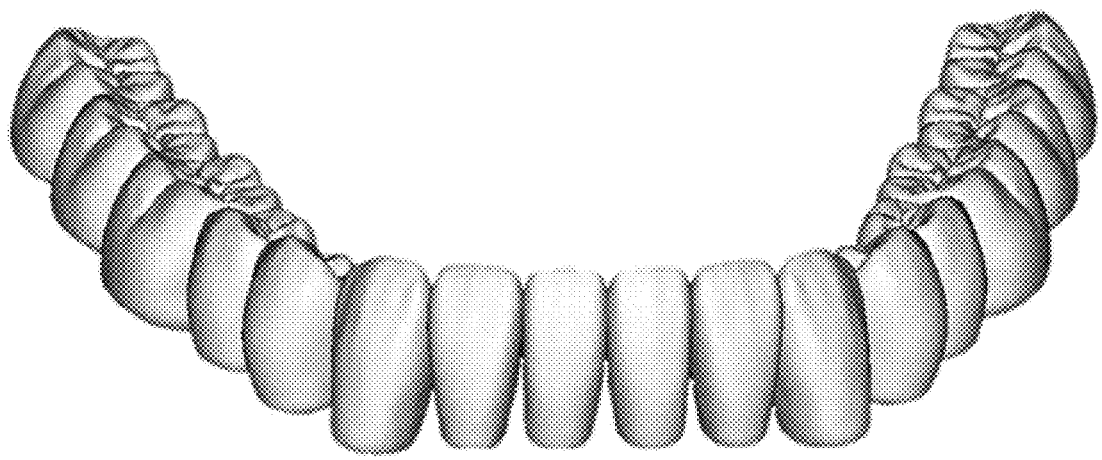
FIG. 3A is a perspective view illustrating an example of the 3D dental library model.
Figure 3B:
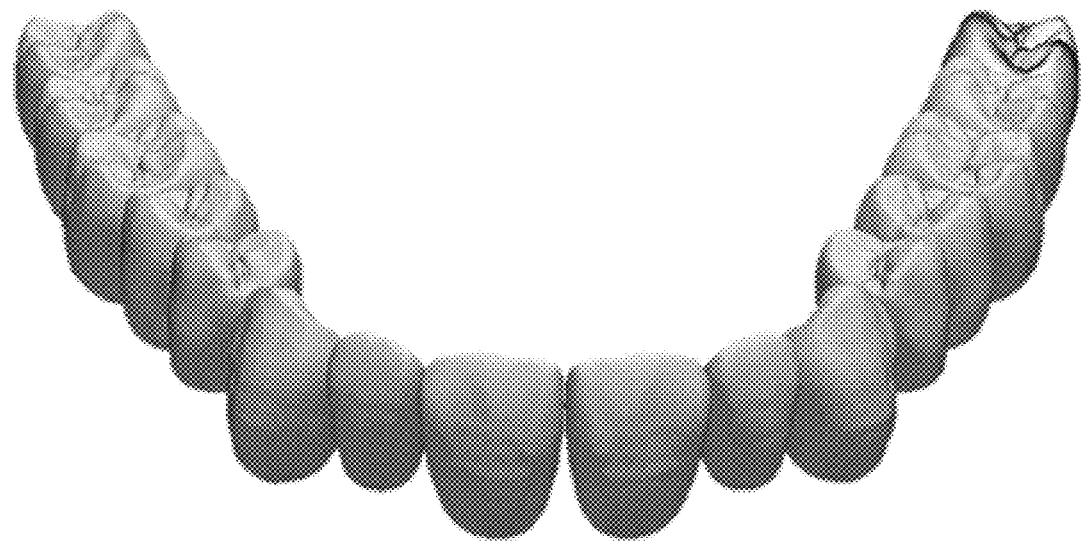
FIG. 3B is a perspective view illustrating an example of the 3D dental library model.

FIG. 1 is a flowchart diagram illustrating an automated method for aligning a three dimensional (3D) dental library model to 3D oral scan data according to an embodiment of the present inventive concept. FIG. 2A is a perspective view illustrating an example of the 3D oral scan data. FIG. 2B is a perspective view illustrating an example of the 3D oral scan data. FIG. 3A is a perspective view illustrating an example of the 3D dental library model. FIG. 3B is a perspective view illustrating an example of the 3D dental library model.

Referring to FIGS. 1 to 3B, the automated method for aligning the 3D dental library model to the 3D oral scan data includes determining a valid tooth of the 3D oral scan data (operation S200), extracting scan landmarks of the 3D oral scan data (operation S300), loading a dental library model corresponding to the valid tooth of the 3D oral scan data (operation S400), extracting library landmarks of the dental library model (operation S500), initial-aligning the dental library model to the 3D oral scan data using the scan landmarks and the library landmarks (operation S600) and matching an individual tooth of the dental library model and an individual tooth of the 3D oral scan data (operation S700). The automated method for aligning the 3D dental library model to the 3D oral scan data may further include receiving the 3D oral scan data (operation S100). The automated method for aligning the 3D dental library model to the 3D oral scan data may further include segmenting teeth of the 3D oral scan data to generate teeth segmentation data (operation S200).

The 3D oral scan data may refer to data scanned by a 3D scanner for teeth and oral cavity, an impression model of the teeth and the oral cavity or a reconstruction model of the teeth and the oral cavity. For example, the 3D oral scan data may be mesh data including 3D vertexes and triangles or rectangles generated by connecting the 3D vertexes. The 3D oral scan data may be image data captured by the 3D scanner. A filename extension of the 3D oral scan data is not limited, and may be, for example, one of ply, obj and stl.

FIGS. 2A and 2B represent examples of the 3D oral scan data. For example, the 3D oral scan data of FIG. 2A may be oral scan data for a mandible and may include all teeth without missing teeth. The 3D oral scan data of FIG. 2B may be oral scan data for a maxilla and may include all teeth except for second premolar.

The dental library model is a kind of sample tooth (a standard tooth) used to manufacture the prostheses, the implants and the braces and may have a typical tooth shape. The dental library model may have one sample tooth (the standard tooth) for each tooth number. The 3D oral scan data are captured by the 3D scanner so that the 3D oral scan data may have a low degree of completion of the mesh. When the degree of the completion of the mesh is low, a 3D printing may be inappropriate for manufacturing the prostheses, the implants and the braces. In contrast, the 3D dental library model may have a high degree of completion of the mesh. Thus, when the prostheses, the implants and the braces are manufactured by deforming the 3D dental library model, the 3D printing may be very suitable for manufacturing the prostheses, the implants and the braces. Accordingly, when the 3D dental library model is aligned with the patient's oral scan data, the 3D dental library model aligned with the oral scan data may be an intermediate model suitable for digitally manufacturing prostheses, implants and braces.

The automated method for aligning the 3D dental library model to the 3D oral scan data of the present embodiment may be operated by a computing apparatus.

FIGS. 3A and 3B represent examples of the 3D dental library model. For example, the 3D dental library model of FIG. 3A may be a dental library model for a mandible. The 3D dental library model of FIG. 3B may be a dental library model for a maxilla.

The operation (operation S200) of determining the valid tooth of the 3D oral scan data and/or segmenting the teeth of the 3D oral scan data may be processed manually by a user or processed automatically through a deep learning. A case in which the operation (operation S200) of determining the valid tooth of the 3D oral scan data and/or segmenting the teeth of the 3D oral scan data is processed automatically through a deep learning is explained later in detail referring to FIG. 11.

The operation (operation S300) of extracting the scan landmarks of the 3D oral scan data may be processed manually by the user or processed automatically through a deep learning. A case in which the operation (operation S300) of extracting the scan landmarks of the 3D oral scan data is processed automatically through a deep learning is explained later in detail referring to FIG. 12. The library landmarks of the 3D dental library model may be pre-stored with the 3D dental library model. In this case, the operation (operation S500) of extracting the library landmarks may be loading the pre-stored library landmarks. Alternatively, the library landmarks may be extracted manually by the user or extracted automatically through a deep learning. A case in which the operation (operation S300) of extracting the scan landmarks of the 3D oral scan data and the operation (operation S500) of extracting the library landmarks of the 3D dental library model are processed automatically through a deep learning is explained later in detail referring to FIG. 13.

Figure 4A:
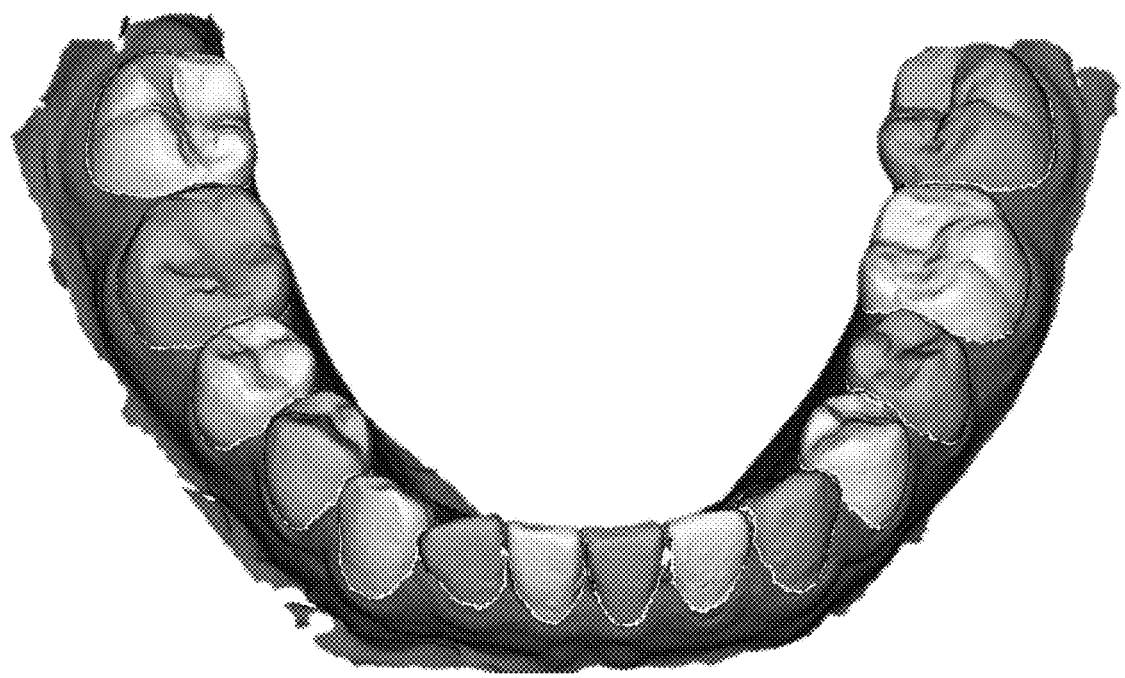
FIG. 4A is a perspective view illustrating an example of first 3D oral scan data with tooth information.
Figure 4B:
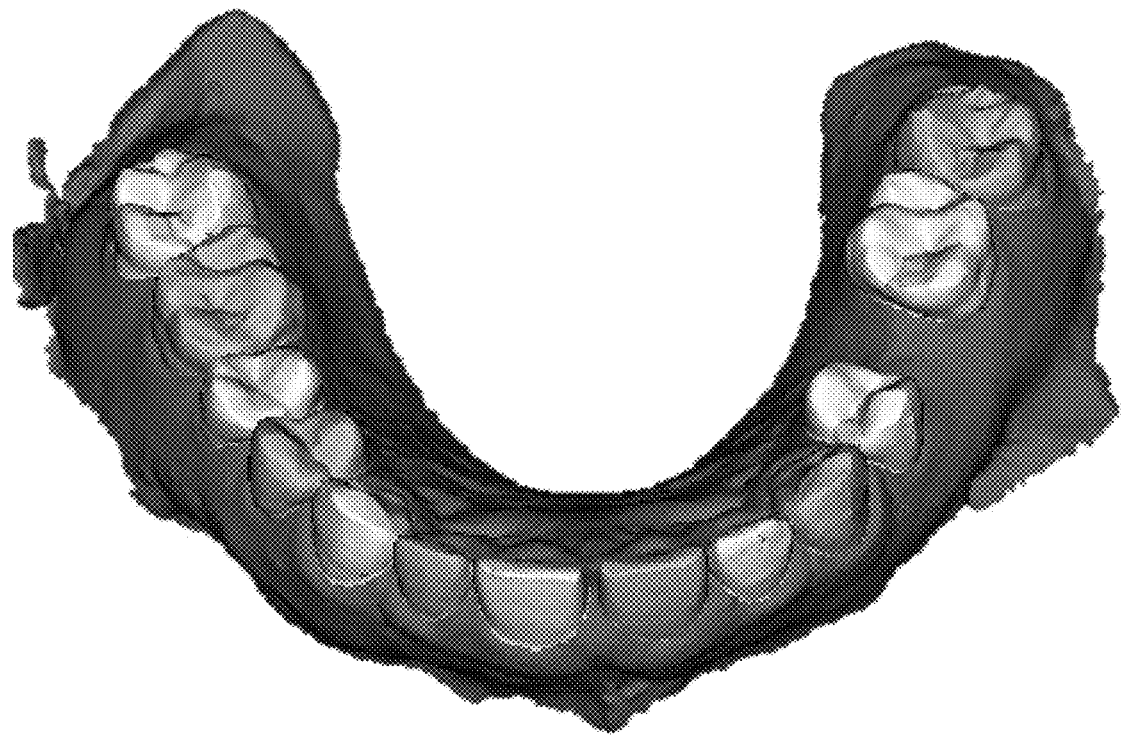
FIG. 4B is a perspective view illustrating an example of second 3D oral scan data with tooth information.
Figure 5A:
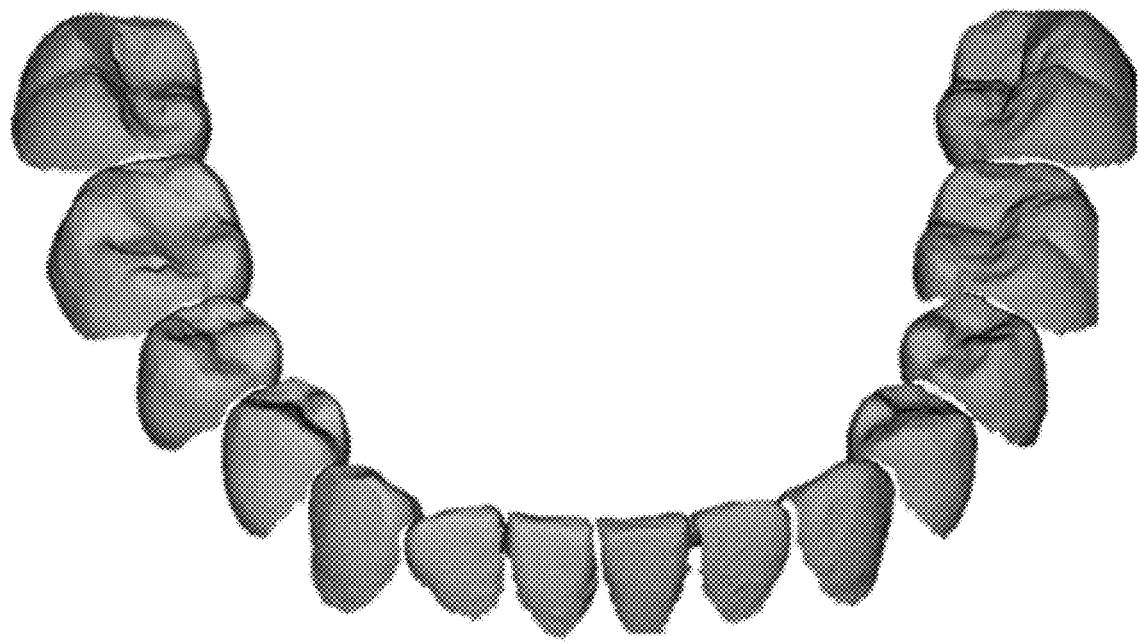
FIG. 5A is a perspective view illustrating an example of teeth extracted from the first 3D oral scan data.
Figure 5B:
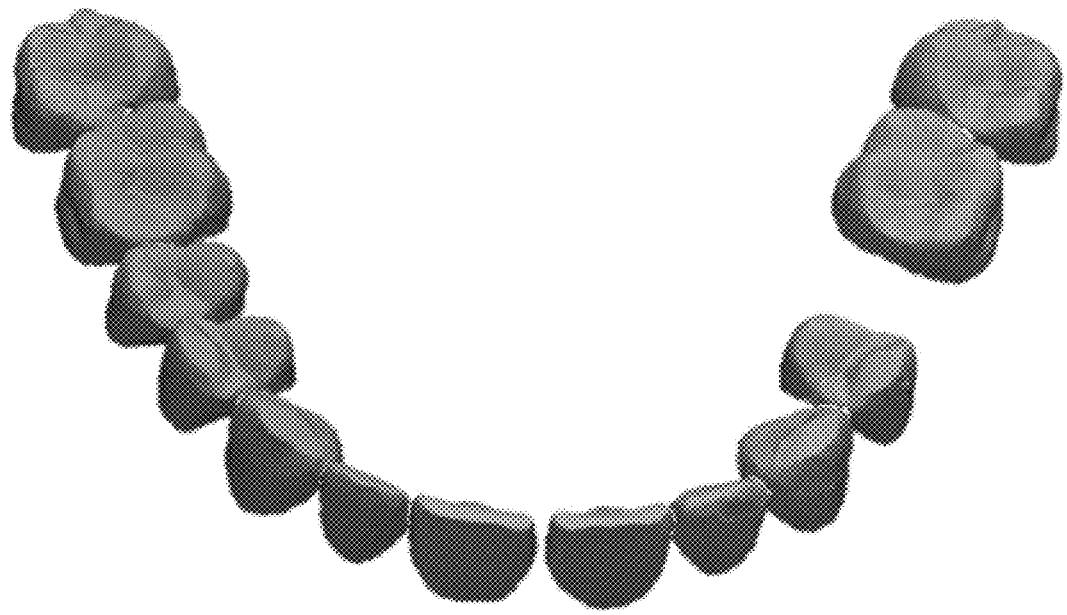
FIG. 5B is a perspective view illustrating an example of teeth extracted from the second 3D oral scan data.

FIG. 4A is a perspective view illustrating an example of first 3D oral scan data with tooth information. FIG. 4B is a perspective view illustrating an example of second 3D oral scan data with tooth information. FIG. 5A is a perspective view illustrating an example of teeth extracted from the first 3D oral scan data. FIG. 5B is a perspective view illustrating an example of teeth extracted from the second 3D oral scan data.

Referring to FIGS. 1 to 5B, the valid tooth of the 3D oral scan data may be determined (operation S200). For example, a tooth type of the valid tooth of the 3D oral scan data may be determined (operation S200). When there is a missing tooth in the 3D oral scan data, the 3D dental library model may not be loaded for the missing tooth. Therefore, the operation of determining the valid tooth of the 3D oral scan data may be preceded.

In the operation (operation S200) of determining the valid tooth of the 3D oral scan data, individual tooth information of each tooth of the 3D oral scan data may be derived. For example, the individual tooth information may include the tooth type (the tooth number), a location, a shape and a boundary between the tooth and gingiva. For example, the individual tooth information may be a scalar value or a labeling value expressed on the 3D oral scan data.

In the operation (operation S200) of determining the valid tooth of the 3D oral scan data, the teeth of the 3D oral scan data may be segmented so that the teeth segmentation data may be generated.

FIG. 4A shows an example in which the individual tooth information is shaded on individual teeth of the first 3D oral scan data. FIG. 4B shows an example in which the individual tooth information is shaded on individual teeth of the second 3D oral scan data.

FIG. 5A illustrates first teeth segmentation data extracted from the first 3D oral scan data. FIG. 5B illustrates second teeth segmentation data extracted from the second 3D oral scan data.

Figure 6A:
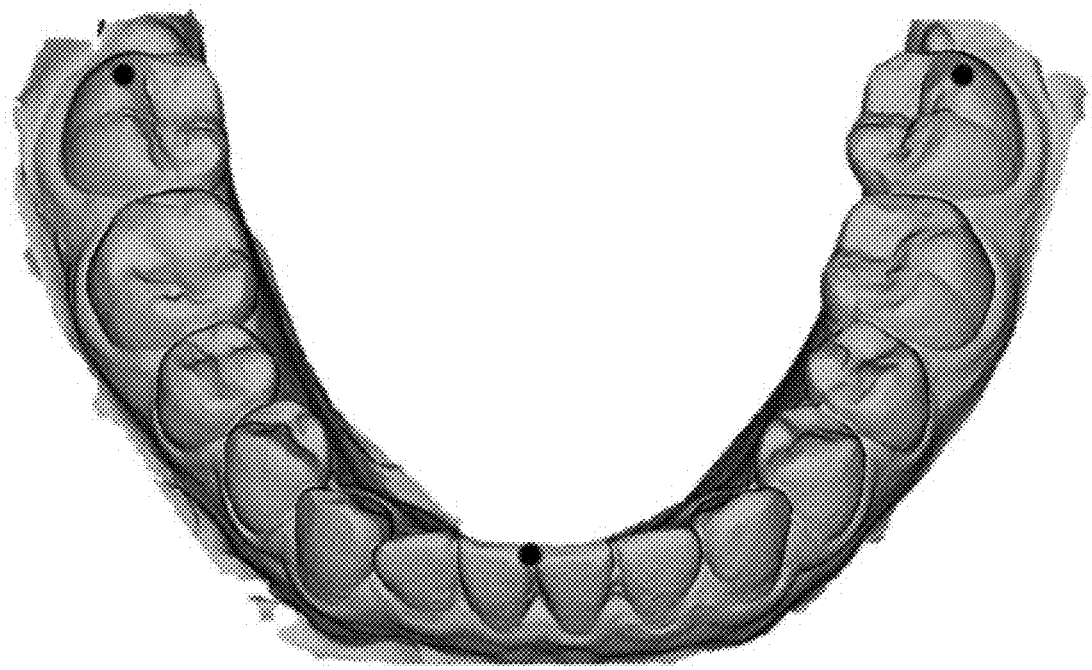
FIG. 6A is a perspective view illustrating an example of the first 3D oral scan data with scan landmarks.
Figure 6B:
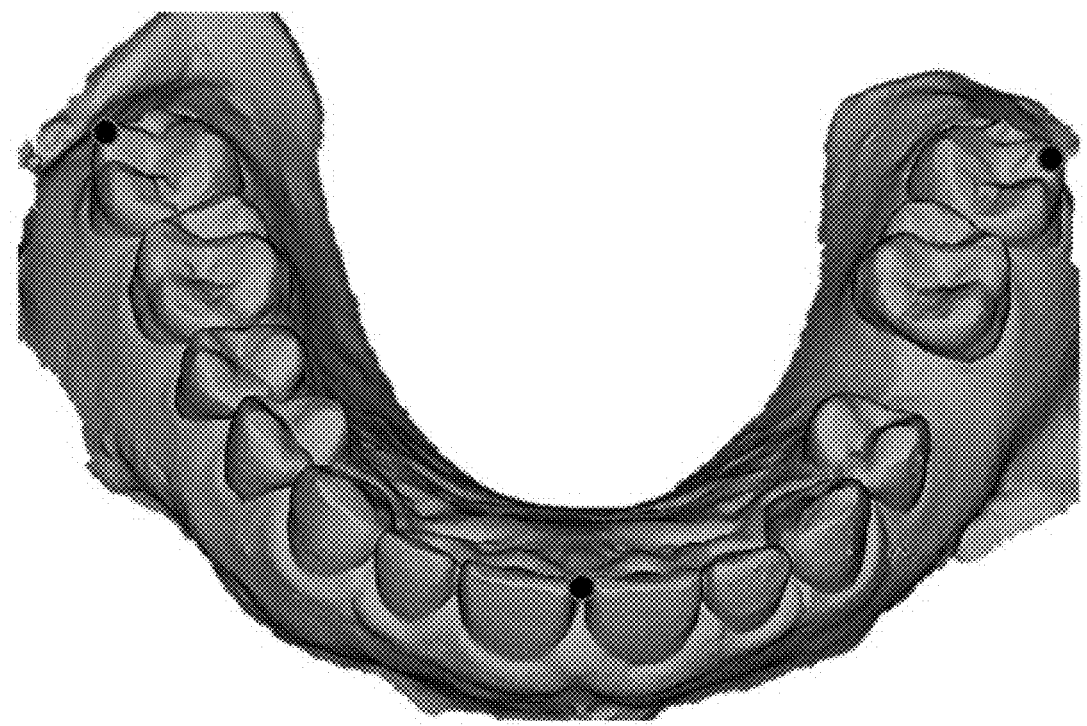
FIG. 6B is a perspective view illustrating an example of the second 3D oral scan data with scan landmarks.
Figure 7A:
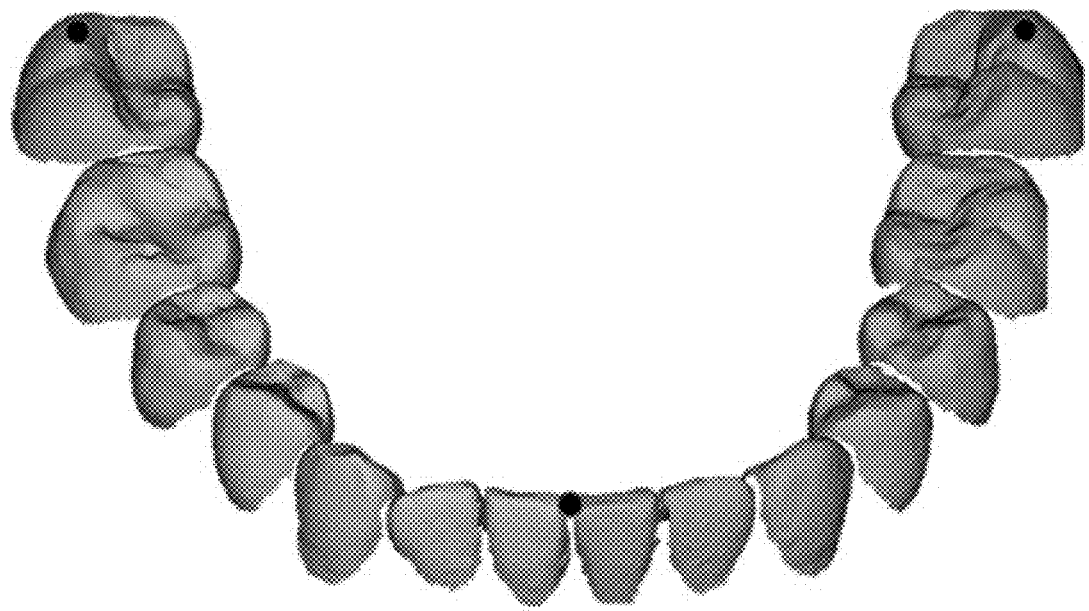
FIG. 7A is a perspective view illustrating teeth segmentation data of the first 3D oral scan data with the scan landmarks.
Figure 7B:
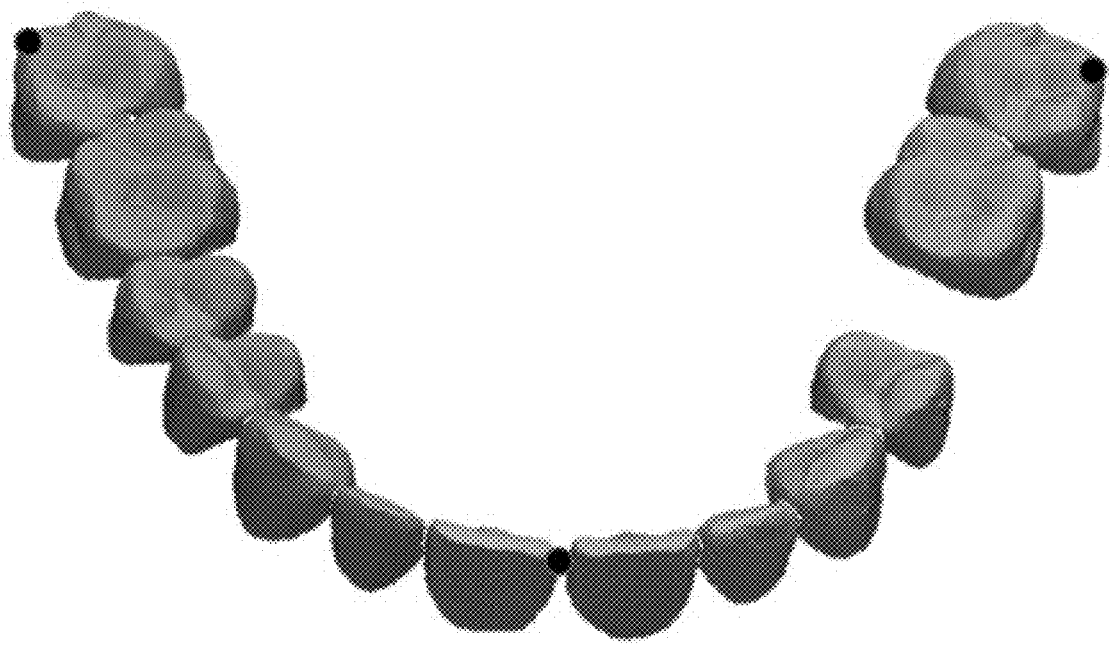
FIG. 7B is a perspective view illustrating teeth segmentation data of the second 3D oral scan data with the scan landmarks.

FIG. 6A is a perspective view illustrating an example of the first 3D oral scan data with scan landmarks. FIG. 6B is a perspective view illustrating an example of the second 3D oral scan data with scan landmarks. FIG. 7A is a perspective view illustrating teeth segmentation data of the first 3D oral scan data with the scan landmarks. FIG. 7B is a perspective view illustrating teeth segmentation data of the second 3D oral scan data with the scan landmarks.

Referring to FIGS. 1 to 7B, the scan landmarks of the 3D oral scan data may be extracted (operation S300). FIG. 6A shows an example of the first 3D oral scan data in which the scan landmarks are illustrated. FIG. 6B shows an example of the second 3D oral scan data in which the scan landmarks are illustrated. FIG. 7A shows an example of first teeth segmentation data in which the scan landmarks are illustrated. FIG. 7B shows an example of second teeth segmentation data in which the scan landmarks are illustrated.

The scan landmarks may include at least three landmarks disposed in the 3D oral scan data. For example, the scan landmarks may be disposed on an upper surface of the teeth, on a lateral surface of the teeth or inside the teeth.

For example, the scan landmarks may include a first landmark disposed at a first end of a first arch formed by the teeth of the 3D oral scan data, a second landmark disposed at a second end of the first arch and a third landmark disposed at a central point of the first arch.

For example, the scan landmarks may include a first landmark disposed at a last tooth in a first end in a horizontal direction of the 3D oral scan data, a second landmark disposed at a last tooth in a second end in the horizontal direction of the 3D oral scan data and a third landmark disposed at a center of two central incisors of the 3D oral scan data.

Figure 8A:
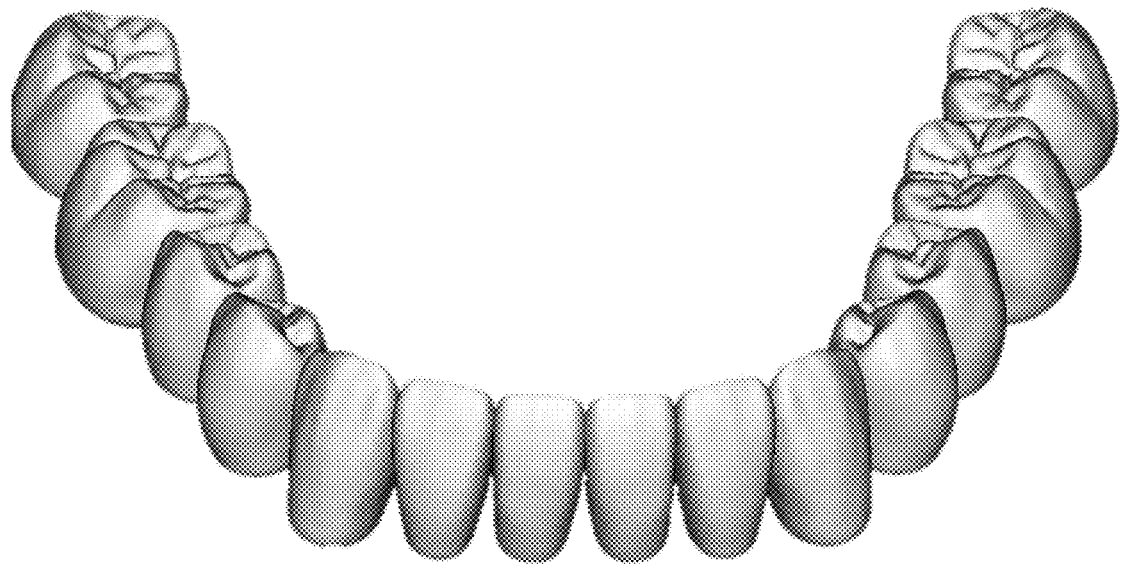
FIG. 8A is a perspective view illustrating a first 3D dental library model corresponding to the first 3D oral scan data.
Figure 8B:
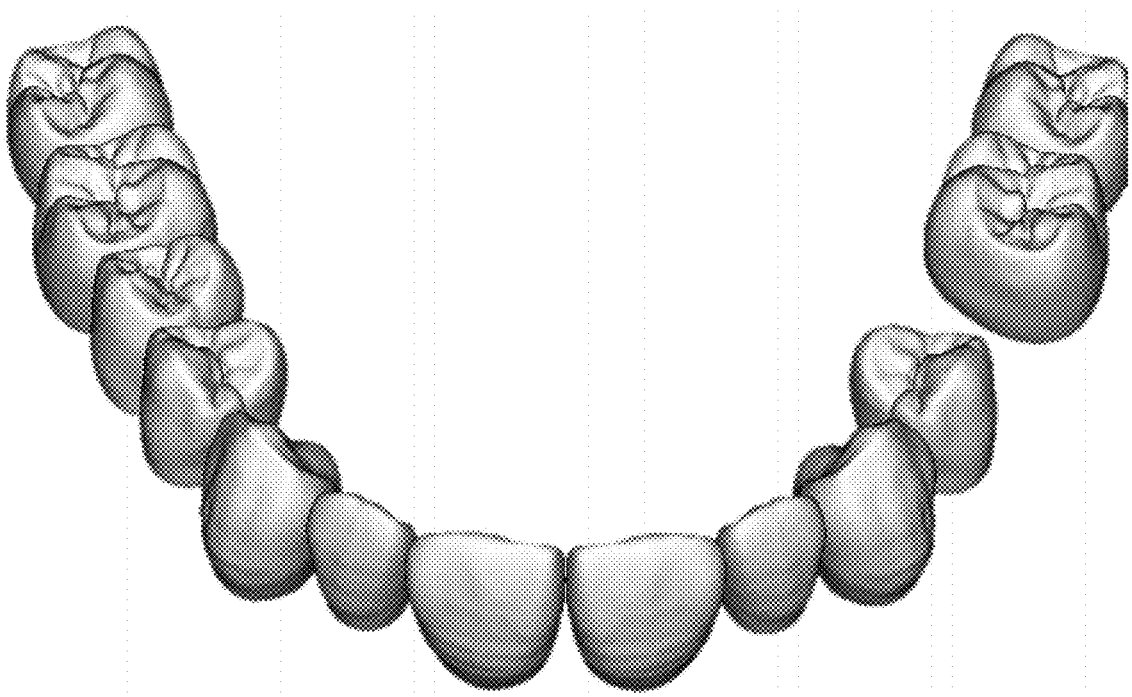
FIG. 8B is a perspective view illustrating a second 3D dental library model corresponding to the second 3D oral scan data.

FIG. 8A is a perspective view illustrating a first 3D dental library model corresponding to the first 3D oral scan data. FIG. 8B is a perspective view illustrating a second 3D dental library model corresponding to the second 3D oral scan data.

Referring to FIGS. 1 to 8B, the dental library model corresponding to the valid tooth of the 3D oral scan data may be loaded (operation S400). For example, when the 3D oral scan data include all teeth, the 3D dental library models of all teeth may be loaded. In contrast, when there is a missing tooth in the 3D oral scan data, the 3D dental library models of all teeth except for the missing tooth may be loaded.

FIG. 8A illustrates the first 3D dental library model corresponding to the first 3D oral scan data of FIG. 2A. FIG. 8B illustrates the second 3D dental library model corresponding to the second 3D oral scan data of FIG. 2B. The second 3D oral scan data of FIG. 2B does not include the second premolar so that the second 3D dental library model does not include a second premolar corresponding to the missing second premolar of the second 3D oral scan data.

Figure 9A:
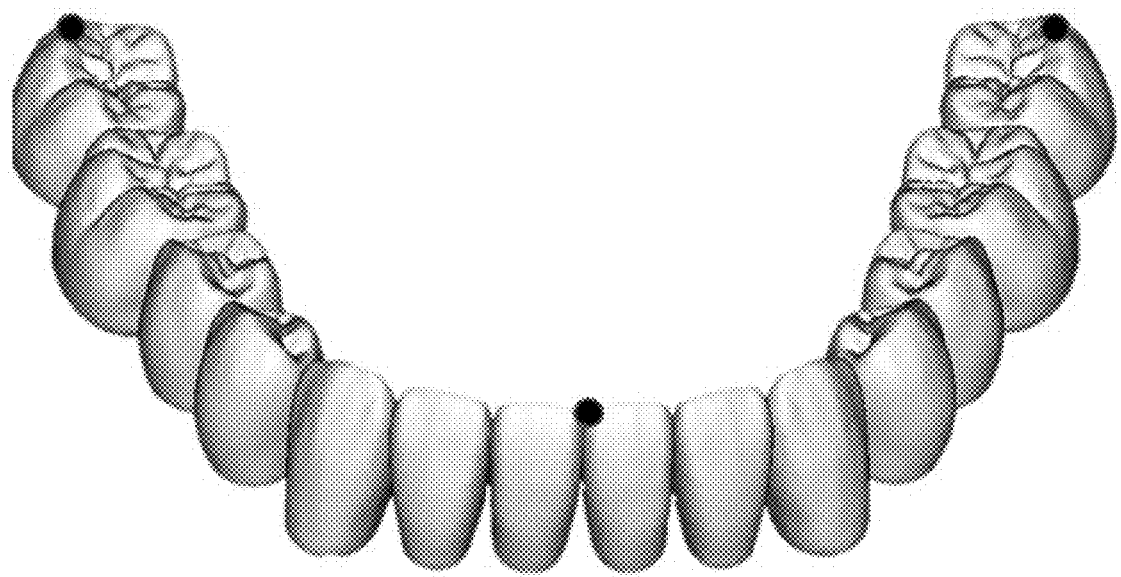
FIG. 9A is a perspective view illustrating the first 3D dental library model with library landmarks.
Figure 9B:
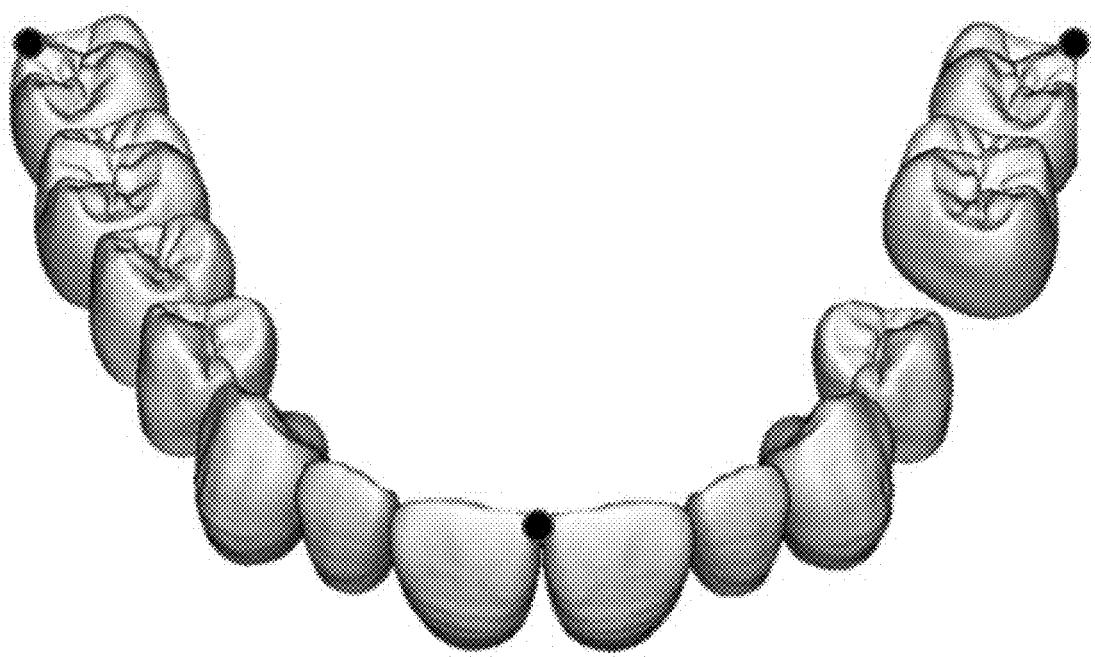
FIG. 9B is a perspective view illustrating the second 3D dental library model with library landmarks.

FIG. 9A is a perspective view illustrating the first 3D dental library model with library landmarks. FIG. 9B is a perspective view illustrating the second 3D dental library model with library landmarks.

Referring to FIGS. 1 to 9B, the library landmarks of the 3D dental library model may be extracted (operation S500). FIG. 9A shows an example of the first 3D dental library model in which the library landmarks are illustrated. FIG. 9B shows an example of the second 3D dental library model in which the library landmarks are illustrated.

The library landmarks may include at least three landmarks disposed in the 3D dental library model. For example, the library landmarks may be disposed on an upper surface of the teeth, on a lateral surface of the teeth or inside the teeth.

For example, the library landmarks may include a fourth landmark disposed at a first end of a second arch formed by the teeth of the 3D dental library model, a fifth landmark disposed at a second end of the second arch and a sixth landmark disposed at a central point of the second arch.

For example, the library landmarks may include a fourth landmark disposed at a last tooth in a first end in a horizontal direction of the 3D dental library model, a fifth landmark disposed at a last tooth in a second end in the horizontal direction of the 3D dental library model and a third landmark disposed at a center of two central incisors of the 3D dental library model.

Figure 10A:
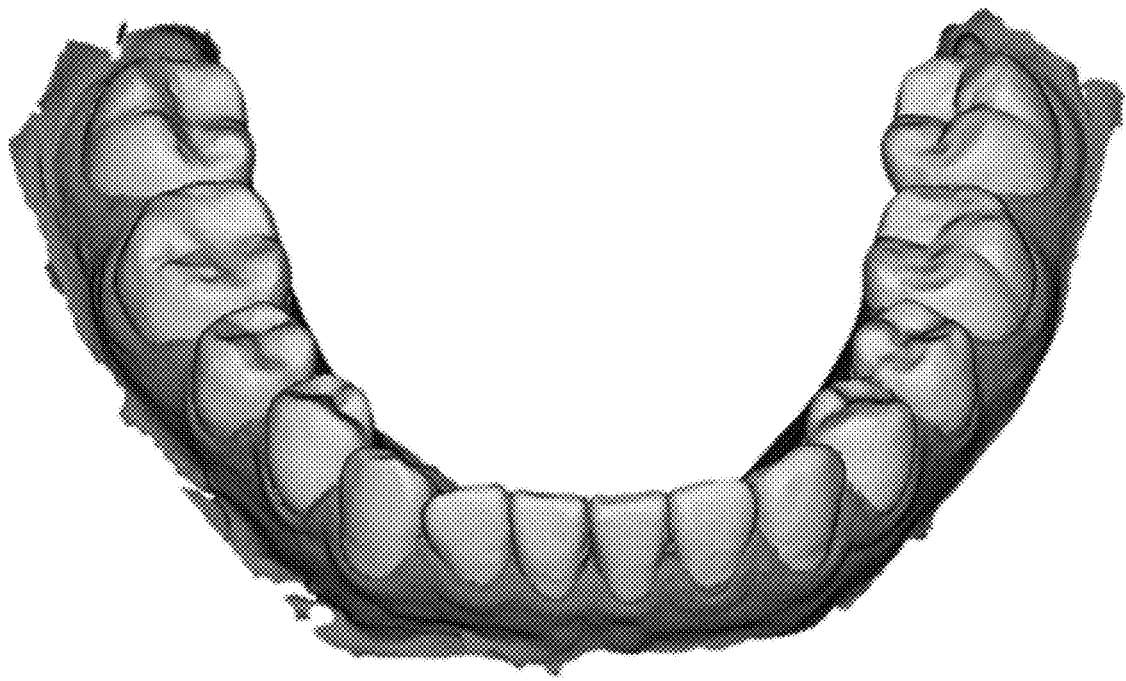
FIG. 10A is a perspective view illustrating the first 3D oral scan data and the first 3D dental library model which are automatically aligned.
Figure 10B:
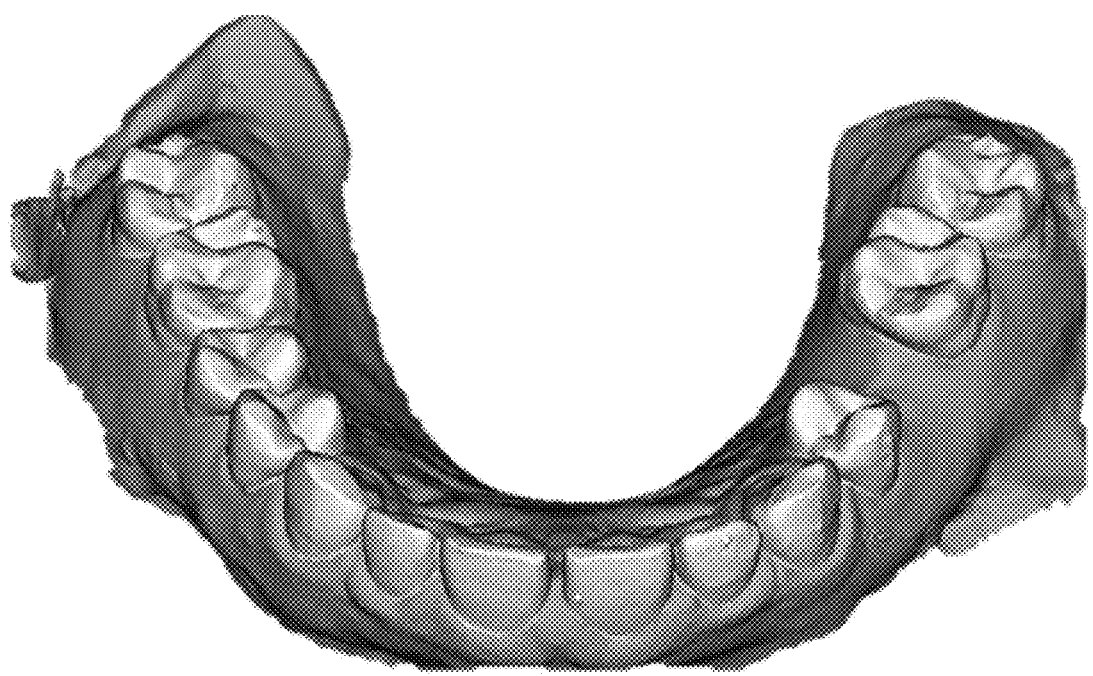
FIG. 10B is a perspective view illustrating the second 3D oral scan data and the second 3D dental library model which are automatically aligned.

FIG. 10A is a perspective view illustrating the first 3D oral scan data and the first 3D dental library model which are automatically aligned. FIG. 10B is a perspective view illustrating the second 3D oral scan data and the second 3D dental library model which are automatically aligned.

Referring to FIGS. 1 to 10B, the 3D dental library model may be initially aligned to the 3D oral scan data using the scan landmarks and the library landmarks (operation S600).

For example, the axes of the 3D dental library model and the axes of the 3D oral scan data may be aligned using the scan landmarks and the library landmarks.

For example, in the operation (operation S600) of initial-aligning the 3D dental library model to the 3D oral scan data, translation, rotation and scaling may be applied to the 3D dental library model. For example, when a distance between the fourth landmark and the fifth landmark of the library landmarks is greater than a distance between the first landmark and the second landmark of the scan landmarks, a size of the dental library model may be reduced as a whole. For example, when the distance between the fourth landmark and the fifth landmark of the library landmarks is less than the distance between the first landmark and the second landmark of the scan landmarks, the size of the dental library model may be enlarged as a whole.

After matching the fourth landmark and the fifth landmark of the library landmarks with the first landmark and the second landmark of the scan landmarks, the sixth landmark of the library landmarks may be matched with the third landmark of the scan landmarks. In this process, the dental library model may be also translated, rotated, or scaled.

For example, in the operation (operation S600) of initial-aligning the 3D dental library model to the 3D oral scan data, the second arch formed by the teeth of the 3D dental library model may be matched with the first arch formed by the teeth of the 3D oral scan data.

When the initial alignment (operation S600) is completed, an individual tooth of the dental library model may be matched with an individual tooth of the 3D oral scan data (operation S700).

The operation (operation S700) of matching the individual tooth of the dental library model with the individual tooth of the 3D oral scan data may include matching a center of the individual tooth of the dental library model with a center of the individual tooth of the 3D oral scan data. In the operation of matching the center of the individual tooth of the dental library model with the center of the individual tooth of the 3D oral scan data, the individual tooth of the dental library model may be moved in parallel.

In the operation (operation S700) of matching the individual tooth of the dental library model with the individual tooth of the 3D oral scan data, the individual tooth of the dental library model may be rotated and a size of the individual tooth of the dental library model may be adjusted so that a difference between an angle of the individual tooth of the dental library model and an angle of the individual tooth of the 3D oral scan data and a difference between the size of the individual tooth of the dental library model and a size of the individual tooth of the 3D oral scan data may be minimized.

In the operation (operation S700) of matching the individual tooth of the dental library model with the individual tooth of the 3D oral scan data, the teeth segmented from the 3D oral scan data and the individual teeth of the dental library model are matched by the tooth types (the tooth numbers) and may be precisely aligned using an iterative closest points (ICP) method and the individual teeth of the dental library model may be resized to fit the segmented teeth.

Figure 11:
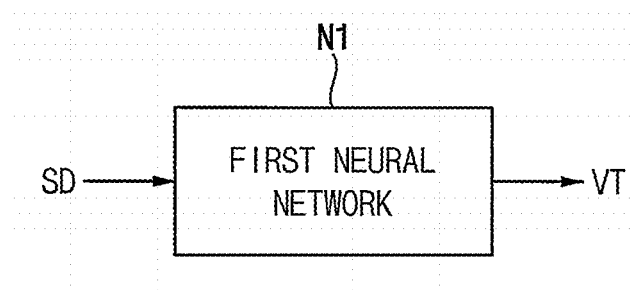
FIG. 11 is a block diagram illustrating a first neural network determining valid tooth from the 3D oral scan data.
Figure 12:
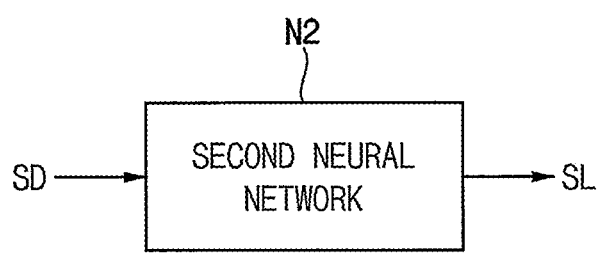
FIG. 12 is a block diagram illustrating a second neural network determining scan landmarks from the 3D oral scan data.

FIG. 11 is a block diagram illustrating a first neural network N1 determining the valid tooth from the 3D oral scan data. FIG. 12 is a block diagram illustrating a second neural network N2 determining the scan landmarks from the 3D oral scan data.

Referring to FIGS. 1 to 12, the first neural network N1 may be used in the operation (operation S200) of determining the valid tooth of the 3D oral scan data and the second neural network N2 different from the first neural network N1 may be used in the operation (operation S300) of extracting the scan landmarks of the 3D oral scan data.

The first neural network N1 and the second neural network may be artificial intelligence neural networks. The first neural network N1 and the second neural network may be convolutional neural networks.

An input of the first neural network N1 may be the 3D oral scan data SD and an output of the first neural network N1 may be the individual tooth information VT of the 3D oral scan data. For example, the individual tooth information VT may be a scalar value or a labeling value expressed on the 3D oral scan data.

Alternatively, the input of the first neural network N1 may be the 3D oral scan data SD and the output of the first neural network N1 may be the teeth segmentation data VT of the 3D oral scan data including segmented teeth of the 3D oral scan data.

An input of the second neural network N2 may be the 3D oral scan data SD and an output of the second neural network N2 may be 3D coordinates of the scan landmarks SL.

Alternatively, the operation (operation S300) of extracting the scan landmarks of the 3D oral scan data SD may include generating a two dimensional (2D) depth image based on the 3D oral scan data SD, extracting 2D coordinates of the scan landmarks SL from the 2D depth image using the second neural network N2 and inverse-projecting the 2D coordinates to the 3D oral scan data SD. Herein, the input of the second neural network N2 may be the 2D depth image generated based on the 3D oral scan data SD and the output of the second neural network N2 may be the 2D coordinates of the scan landmarks SL.

Figure 13:
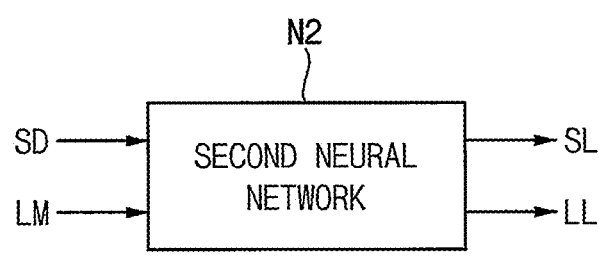
FIG. 13 is a block diagram illustrating a second neural network determining scan landmarks from the 3D oral scan data and library landmarks from the 3D dental library model.

FIG. 13 is a block diagram illustrating a second neural network N2 determining scan landmarks from the 3D oral scan data and library landmarks from the 3D dental library model.

According to the present embodiment, both the scan landmarks of the 3D oral scan data and the library landmarks of the 3D dental library model may be extracted by the second neural network N2.

Inputs of the second neural network N2 may be the 3D oral scan data SD and the 3D dental library model LM and outputs of the second neural network N2 may be the 3D coordinates of the scan landmarks SL and the 3D coordinates of the library landmarks LL.

Alternatively, the operation (operation S300) of extracting the scan landmarks of the 3D oral scan data SD may include generating a two dimensional (2D) depth image based on the 3D oral scan data SD, extracting 2D coordinates of the scan landmarks SL from the 2D depth image and inverse-projecting the 2D coordinates to the 3D oral scan data SD. Herein, the input of the second neural network N2 may be the 2D depth image generated based on the 3D oral scan data SD and the output of the second neural network N2 may be the 2D coordinates of the scan landmarks SL.

In addition, the operation (operation S500) of extracting the library landmarks of the 3D dental library model LM may include generating a 2D depth image based on the 3D dental library model LM, extracting 2D coordinates of the library landmarks LL from the 2D depth image and inverse-projecting the 2D coordinates to the 3D dental library model LM. Herein, the input of the second neural network N2 may be the 2D depth image generated based on the 3D dental library model LM and the output of the second neural network N2 may be the 2D coordinates of the library landmarks LL.

According to the present embodiment, the process of aligning the 3D dental library model to the 3D oral scan data is performed automatically so that a work fatigue of the dentist or dental technician may decrease and an accuracy of the aligning result may increase.

In addition, the aligned dental library model may be used to manufacture prostheses, implants, braces and dental instruments so that an effort and a time of manufacturing the prostheses, the implants, the braces and the dental instruments may decrease and an accuracy and a productivity of the prostheses, the implants, the braces and the dental instruments may increase.

In addition, a deep learning may be used in some steps of the automated method for aligning the 3D dental library model to the 3D oral scan data. When the deep learning is be used in some steps, the work fatigue of the dentist or dental technician may further decrease and the accuracy of the aligning result may further increase.

According to an embodiment of the present inventive concept, a non-transitory computer-readable storage medium having stored thereon program instructions of the automated method for aligning the 3D dental library model to the 3D oral scan data may be provided. The above mentioned method may be written as a program executed on the computer. The method may be implemented in a general purpose digital computer which operates the program using a computer-readable medium. In addition, the structure of the data used in the above mentioned method may be written on a computer readable medium through various means. The computer readable medium may include program instructions, data files and data structures alone or in combination. The program instructions written on the medium may be specially designed and configured for the present inventive concept, or may be generally known to a person skilled in the computer software field. For example, the computer readable medium may include a magnetic medium such as a hard disk, a floppy disk and a magnetic tape, an optical recording medium such as CD-ROM and DVD, a magneto-optical medium such as floptic disc and a hardware device specially configured to store and execute the program instructions such as ROM, RAM and a flash memory. For example, the program instructions may include a machine language codes produced by a compiler and high-level language codes which may be executed by a computer using an interpreter or the like. The hardware device may be configured to operate as one or more software modules to perform the operations of the present inventive concept.

In addition, the above mentioned automated method for aligning the 3D dental library model to the 3D oral scan data may be implemented in a form of a computer-executed computer program or an application which are stored in a storage method.

The present inventive concept is related to the automated method for aligning the 3D dental library model to the 3D oral scan data and the non-transitory computer-readable storage medium having stored thereon program instructions of the automated method for aligning the 3D dental library model to the 3D oral scan data. According to the present inventive concept, an effort and a time of manufacturing the prostheses, the implants, the braces and the dental instru-ments may decrease and an accuracy and a productivity of the prostheses, the implants, the braces and the dental instruments may increase.

The foregoing is illustrative of the present inventive concept and is not to be construed as limiting thereof. Although a few embodiments of the present inventive concept have been described, those skilled in the art will readily appreciate that many modifications are possible in the embodiments without materially departing from the novel teachings and advantages of the present inventive concept. Accordingly, all such modifications are intended to be included within the scope of the present inventive concept as defined in the claims. In the claims, means-plus-function clauses are intended to cover the structures described herein as performing the recited function and not only structural equivalents but also equivalent structures. Therefore, it is to be understood that the foregoing is illustrative of the present inventive concept and is not to be construed as limited to the specific embodiments disclosed, and that modifications to the disclosed embodiments, as well as other embodiments, are intended to be included within the scope of the appended claims. The present inventive concept is defined by the following claims, with equivalents of the claims to be included therein.

What is claimed is:

1. An automated method for aligning a 3D dental library model to 3D oral scan data, the method comprising:
    determining a valid tooth of the 3D oral scan data;
    extracting scan landmarks of the 3D oral scan data;
    loading the 3D dental library model corresponding to the valid tooth of the 3D oral scan data;
    extracting library landmarks of the 3D dental library model;
    initial-aligning the 3D dental library model to the 3D oral scan data using the scan landmarks and the library landmarks; and
    matching an individual tooth of the 3D dental library model and an individual tooth of the 3D oral scan data,
    wherein the extracting the scan landmarks of the 3D oral scan data comprises:
    generating a 2D depth image based on the 3D oral scan data;
    extracting 2D coordinates of the scan landmarks from the 2D depth image; and
    inverse-projecting the 2D coordinates to the 3D oral scan data.

2. The method of claim 1, further comprising segmenting teeth of the 3D oral scan data to generate teeth segmentation data.

3. The method of claim 1, wherein the initial-aligning the 3D dental library model to the 3D oral scan data comprises:
    matching a second arch formed by teeth of the 3D dental library model with a first arch formed by teeth of the 3D oral scan data.

4. The method of claim 1, wherein the scan landmarks include at least three landmarks disposed in the 3D oral scan data, and
    wherein the library landmarks include at least three landmarks disposed in the 3D dental library model.

5. The method of claim 4, wherein the scan landmarks include a first landmark disposed at a first end of a first arch formed by teeth of the 3D oral scan data, a second landmark disposed at a second end of the first arch and a third landmark disposed at a central point of the first arch, and
    wherein the library landmarks include a fourth landmark disposed at a first end of a second arch formed by teeth of the 3D dental library model, a fifth landmark disposed at a second end of the second arch and a sixth landmark disposed at a central point of the second arch.

6. The method of claim 4, wherein the scan landmarks include a first landmark disposed at a last tooth in a first end in a horizontal direction of the 3D oral scan data, a second landmark disposed at a last tooth in a second end in the horizontal direction of the 3D oral scan data and a third landmark disposed at a center of two central incisors of the 3D oral scan data, and
wherein the library landmarks include a fourth landmark disposed at a last tooth in a first end in a horizontal direction of the 3D dental library model, a fifth landmark disposed at a last tooth in a second end in the horizontal direction of the 3D dental library model and a third landmark disposed at a center of two central incisors of the 3D dental library model.

7. The method of claim 1, wherein the matching the individual tooth of the 3D dental library model and the individual tooth of the 3D oral scan data comprises:
matching a center of the individual tooth of the 3D dental library model with a center of the individual tooth of the 3D oral scan data.

8. The method of claim 7, wherein the matching the individual tooth of the 3D dental library model and the individual tooth of the 3D oral scan data comprises:
rotating the individual tooth of the 3D dental library model and adjusting a size of the individual tooth of the 3D dental library model to minimize a difference between an angle of the individual tooth of the 3D dental library model and an angle of the individual tooth of the 3D oral scan data and a difference between the size of the individual tooth of the 3D dental library model and a size of the individual tooth of the 3D oral scan data.

9. The method of claim 1, wherein a first neural network is used in the determining the valid tooth of the 3D oral scan data, and
wherein a second neural network different from the first neural network is used in the extracting the scan landmarks of the 3D oral scan data.

10. The method of claim 9, wherein an input of the first neural network is the 3D oral scan data and an output of the first neural network is individual tooth information of the 3D oral scan data.

11. The method of claim 10, wherein the individual tooth information is a scalar value or a labeling value expressed on the 3D oral scan data.

12. The method of claim 9, wherein an input of the first neural network is the 3D oral scan data and an output of the first neural network is teeth segmentation data of the 3D oral scan data including segmented teeth of the 3D oral scan data.

13. The method of claim 9, wherein an input of the second neural network is the 3D oral scan data and an output of the second neural network is 3D coordinates of the scan landmarks.

14. The method of claim 9, wherein the second neural network is used in the extracting the library landmarks of the 3D dental library model.

15. A non-transitory computer-readable storage medium having stored thereon program instructions, which when executed by at least one hardware processor, performs the method of claim 1.

* * * * *